United States Patent [19]

Usui et al.

[11] 4,119,777
[45] Oct. 10, 1978

[54] THIAZINE PRODUCTION

[75] Inventors: Hideo Usui; Sadao Ishige, both of Minami Ashigara; Keiso Saeki, Fujimiya, all of Japan

[73] Assignee: Fuji Photo Film Co., Ltd., Minami Ashigara, Japan

[21] Appl. No.: 751,874

[22] Filed: Dec. 17, 1976

[30] Foreign Application Priority Data

Dec. 23, 1975 [JP] Japan .................... 50/153706

[51] Int. Cl.$^2$ .................... C07D 279/14; C07D 279/16
[52] U.S. Cl. .................... 544/6; 544/14; 544/32; 544/34; 544/35; 544/48; 544/50; 542/401; 542/430; 542/469
[58] Field of Search ............... 260/243 R; 544/14, 47, 544/48, 50, 6, 32, 34, 35, ; 542/401, 430, 469

[56] References Cited

U.S. PATENT DOCUMENTS

| | | | |
|---|---|---|---|
| 3,417,085 | 12/1968 | Kuch et al. | 260/243 |
| 3,502,666 | 3/1970 | Kuch et al. | 260/243 |
| 3,586,675 | 6/1971 | Ritchie et al. | 260/243 |

OTHER PUBLICATIONS

Chemical Abstracts, vol. 68, entry 21941(b) 1968.
Chemical Abstracts, vol. 70, entry 87829(u) 1969.

Primary Examiner—John M. Ford
Attorney, Agent, or Firm—Sughrue, Rothwell, Mion, Zinn and Macpeak

[57] ABSTRACT

A thiazine derivative, which forms a color on contact with an electron accepting material, represented by the formula (II):

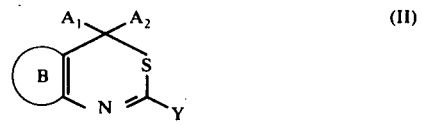

wherein $A_1$ and $A_2$, which may be the same or different, each represents an aryl group or a heterocyclic group and $A_1$ and $A_2$ may combine together to form a heterocyclic ring or a fluorene ring, the ring B represents an aromatic hydrocarbon ring or a heterocyclic ring, and Y represents a hydrogen atom, an aliphatic group, an aryl group, a heterocyclic group, an amino group, an amido group, an oxy group or a thio group, but at least one of $A_1$ and $A_2$ or the ring formed by the combination of $A_1$ and $A_2$ represents an electron donating aryl group or an electron donating heterocyclic group, and a process for preparing the thiazine derivatives represented by the formula (II) by oxidizing a thioamide derivative represented by the formula (I):

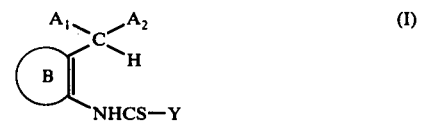

wherein $A_1$, $A_2$, B and Y are as above described.

9 Claims, No Drawings

THIAZINE PRODUCTION

BACKGROUND OF THE INVENTION

1. Field of the Invention

The present invention relates to novel thiazine derivatives which form a color on intimate contact with electron accepting materials and to a process for preparing the same.

2. Description of the Prior Art

Hitherto, 4H-3,1-benzothiazine derivatives represented by the following formula (III) are known as thiazine derivatives, which have been synthesized for use as sedatives (*Chemical Abstracts*, 70, 87829u):

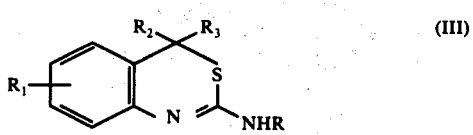

wherein R represents hydrogen, methyl, ethyl, isopropyl, β-diethylaminoethyl, benzyl or benzoyl, $R_1$ represents hydrogen or chlorine, and $R_2$ and $R_3$ each represents methyl, ethyl, propyl or phenyl.

The 4H-3,1-benzothiazine derivatives represented by the formula (III) do not form a color when they contact an electron accepting material, because $R_2$ or $R_3$ in the formula is not an electron donating aryl group such as a p-dimethylaminophenyl group. The compounds represented by the formula (III) are synthesized according to the following reaction schematic (1) or (2).

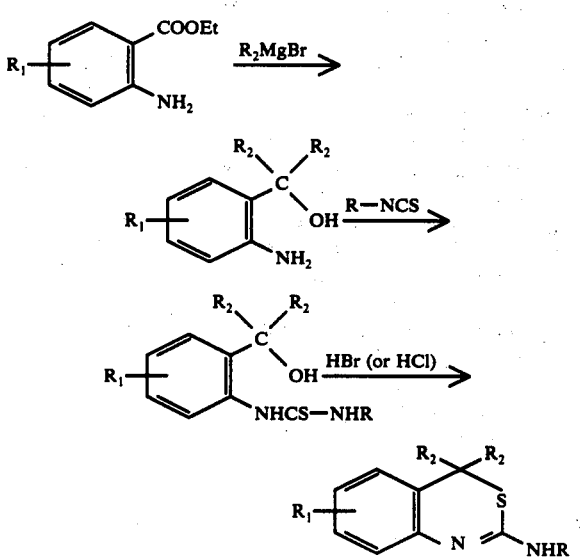

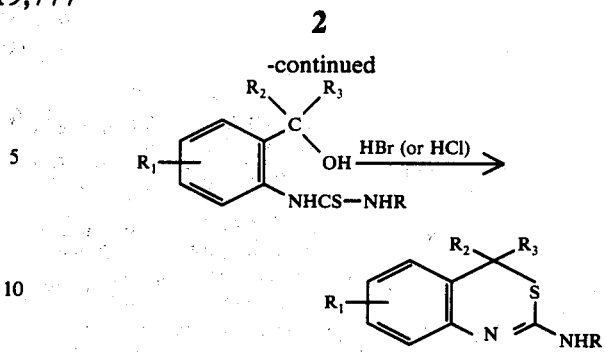

This process is carried out by reacting an o-amino-α,α-disubstituted benzyl alcohol prepared by a Grignard reaction with a thioisocyanate and then ring-closing the synthesized o-thioureido-α,α-disubstituted benzyl alcohol thus obtained by means of hydrogen bromide or hydrogen chloride to yield 4H-3,1-benzothiazine derivatives. The first problem of this process is to utilize the Grignard reaction. Moisture severely affects the Grignard reaction and thus ethers should be used which give rise to the danger of fire. Therefore, the Grignard reaction is very disadvantageous economically, because special production equipment is necessary in industrial operation.

The second problem is that the corresponding o-amino-α,α-disubstituted benzyl alcohol is very unstable and easily forms anhydro-base according to the following reaction schematic (3) where $R_2$ and $R_3$ in the reaction schematic (1) or (2) is each a p-dimethylaminophenyl group and $R_1$ is, for example, a dimethylamino group and, consequently, a thioureido group is difficult to introduce.

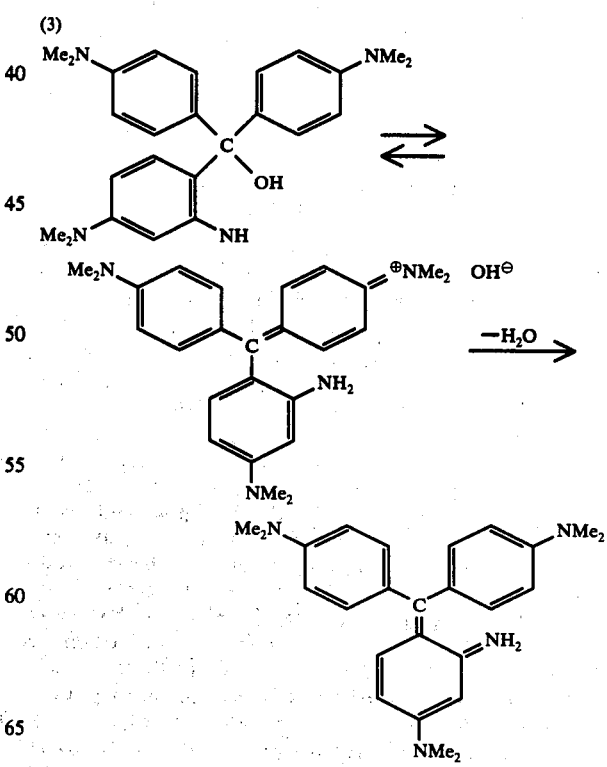

where Me represents a $CH_3$ group.

SUMMARY OF THE INVENTION

Accordingly, a first object of the present invention is to provide novel thiazine derivatives which form a color upon intimate contact with electron accepting materials.

A second object of the present invention is to provide an advantageous process for producing these thiazine derivatives without solvents which are fire hazards or special equipment for production being required.

The above described objects of the present invention have been attained by thiazine derivatives represented by the following formula (II):

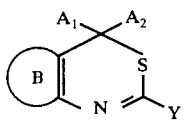

wherein $A_1$ and $A_2$, which may be the same or different, each represents an aryl group or a heterocyclic ring, and $A_1$ and $A_2$ may combine to form a heterocyclic ring or a fluorene ring, the ring B represents an aromatic hydrocarbon ring or a heterocyclic ring, and Y represents a hydrogen atom, an aliphatic group, an aryl group, a heterocyclic group, an amino group, an amido group, an oxy group or a thio group, but at least one of $A_1$ and $A_2$ or the ring formed by the combination of $A_1$ and $A_2$ represents an electron donating aryl group or an electron donating heterocyclic group.

In another embodiment of this invention, this invention provides a process for preparing the thiazine derivatives of the formula (II) by oxidizing thioamide derivatives of the formula (I):

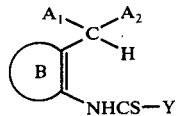

wherein $A_1$, $A_2$, B and Y are as defined above.

DETAILED DESCRIPTION OF THE INVENTION

In the formula (I) and (II), $A_1$ and $A_2$ each represents an aryl group (for example, a phenyl, naphthyl, biphenyl, substituted phenyl, substituted naphthyl or substituted biphenyl group, wherein examples of substituents include one or more alkyl groups (such as methyl, ethyl, propyl, butyl or cyclohexyl, etc.), fluoroalkyl groups (such as trifluoromethyl), aralkyl groups (such as α-methylbenzyl, α,α-dimethylbenzyl, 1,1-diphenylethyl, naphthylmethyl or phenethyl, etc.), halogen atoms (such as fluorine, chlorine, bromine or iodine), alkoxy groups (such as methoxy, ethoxy, propoxy, butoxy or cyclohexyloxy, etc.), aralkyloxy, groups (such as phenethyloxy, benzyloxy or naphthylmethyloxy, etc.), aryloxy groups (such as phenoxy or naphthoxy, etc.), heteroaryloxy groups (such as α-pyridyloxy, γ-pyridyloxy, α-furyloxy, β-furyloxy, α-thienyloxy, β-thienyloxy, 2-pyrimidinyloxy or 2-triazynyloxy, etc.), alkenyloxy groups (such as allyloxy or isopropenyloxy, etc.), alkynyloxy groups (such as ethynyloxy or propargyloxy, etc.), substituted alkoxy groups (such as acetonyloxy, phenacyloxy, ethoxycarbonylmethyloxy, N,N-diethylcarbamoylmethyloxy, acetonylmethyloxy, β-ethoxycarbonylethyloxy, β-(N,N-dimethylamino)ethyloxy, β-methoxyethyloxy, β-cyanoethyloxy, β-chloroethyloxy or β-methanesulfonylethyloxy, etc.), acyloxy groups (such as acetoxy, benzoyloxy, 2-pyridinecarbonyloxy or ethoxycarbonyloxy, etc.), sulfonyloxy groups (such as methanesulfonyloxy or p-toluenesulfonyloxy, etc.), amino groups (such as amino, anilino, ethylamino, benzylamino, allylamino, propargylamino, cyclohexylamino, acetonylamino, ethoxycarbonylmethylamino, β-methoxyethylamino, dimethylamino, diethylamino, dibenzylamino, bis(ethoxymethyl)amino, bis(β-chloroethyl)amino, bis(β-cyanoethyl)amino, N-benzyl-N-ethylamino, N-ethyl-N-(p-tolyl)amino, N-benzyl-N-(β-ethoxyethyl)amino, N-methyl-N-phenacylamino, morpholino, piperidino, pyrrolidino, α-pyridylamino, β-furylamino, α-thienylamino or 2-pyrimidinylamino, etc.), amido groups (such as acetamido, benzamido, α-pyridinecarboxamido, butoxycarbonylamino, 3,3-diethylureido, N-ethylacetamido, p-toluenesulfonamido, N-butylmethanesulfonamido, benzothioamido or 3,3-diethylthioureido, etc.) and thio groups (such as methylthio, ethylthio, butylthio or benzylthio, etc.)) or a heterocyclic group (for example, a 5- or 6-membered heterocyclic ring containing at least one of a nitrogen, oxygen and sulfur atom as a hetero atom, such as p-julolidyl, 1,2,3,4-tetrahydroquinolin-6-yl, 3,3-dimethylindolin-5-yl, 3,4-methylenedioxyphenyl, 1,2-dimethyl-5-benzimidazolyl, 10-ethylphenothiazin-3-yl, 10-ethylphenoxazin-3-yl, 9-ethylcarbazol-3-yl, dibenzofuran-3-yl, dibenzothiophen-3-yl, quinolin-8-yl, 1,2-dimethylindol-3-yl, 1-ethylimidazol-3-yl, benzo[b]furan-3-yl, benzo[b]thiophen-3-yl, 1-ethylpyrrol-3-yl, 3-furyl, 3-thienyl, 2-thiazolyl, 2-benzoxazolyl, 2-pyridyl or 4-quinolyl, etc., wherein the above described heterocyclic ring may have one or more of the same substituents as described in the above described aryl group in $A_1$ and $A_2$). Further, $A_1$ and $A_2$ may combine to form a heterocyclic ring (for example, 9H-xanthene(1), 10-substituted-9,10-dihydroacridine(2), 9H-thioxanthene(3), 1-substituted-4H-chromeno(2,3-c)pyrazole(4), 11H-benzo(b)thieno(3,2-b)chromene(5), 6-substituted-5-oxo-5,6-dihydro-12H-chromeno(2,3-c)isoquinoline(6), 4H-chromene(7) or 2H-chromene(8), wherein the heterocyclic ring may be substituted with one or more of the same substituents, with the numerals in parentheses indicating the formula thereof as shown below:

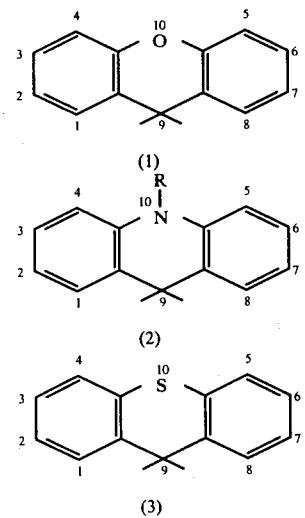

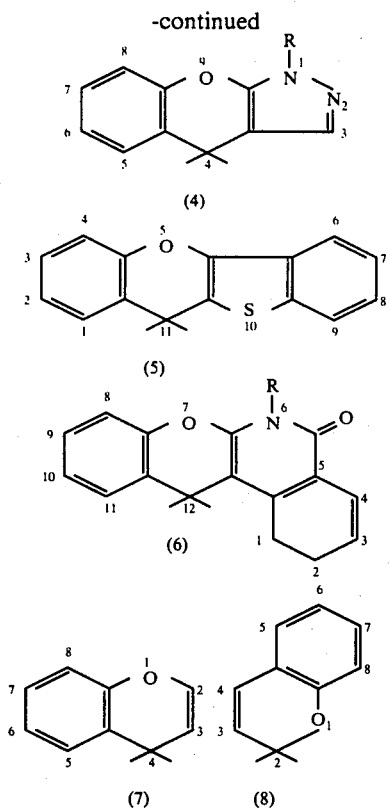

as described in the above described aryl group in $A_1$ or $A_2$) or a fluorene ring (which may be substituted with one or more of the same substituents as described in the above described aryl group in $A_1$ or $A_2$) by linking together. R in the above described heterocyclic rings represents an alkyl group (for example, straight or branched alkyl having 1 to 4 carbon atoms), an aralkyl group (for example, benzyl or phenethyl) or an aryl group (for example, phenyl).

The ring B represents an aromatic hydrocarbon ring (for example, benzene, naphthalene, biphenyl or tetralin, etc., which may be substituted with one or more of the same substituents as described in the above described aryl group in $A_1$ or $A_2$) or a heterocyclic ring (for example, a 5- or 6-membered heterocyclic ring containing at least one of a nitrogen, oxygen and sulfur atom as a hetero atom, such as pyrrole, furan, thiophene, indole, benzofuran, benzothiophene, carbazole, dibenzofuran, dibenzothiophene, julolidine, tetrahydroquinoline, benzimidazole, benzoxazole, benzothiazole or 1,3-benzo[d]dioxole, etc., which may be substituted with one or more of the same substituents as described in the above described aryl group in $A_1$ and $A_2$).

Y represents a hydrogen atom, an aliphatic group (for example, a substituted or unsubstituted alkyl group (for example, straight or branched acyclic alkyl or cycloalkyl having 1 to 18 carbon atoms, such as methyl, ethyl, propyl, butyl, hexyl, octyl, dodecyl, octadecyl, cyclopentyl or cyclohexyl, etc., which may be substituted with one or more of a halogen, alkoxy, dialkylamino or cyano, etc., group), an aralkyl group (for example, benzyl, α-methylbenzyl, α,α-dimethylbenzyl, 1,1-diphenylethyl, naphthylmethyl or phenethyl, etc.), an alkenyl group (for example, allyl, isopropenyl, 2-butenyl, cyclohexenyl or cinnamyl, etc.), or an alkynyl group (for example, ethynyl, propargyl or 2-butynyl, etc.), etc.), an aryl group (which is the same as that described in $A_1$ or $A_2$), a heterocyclic group (which is the same as that described in $A_1$ or $A_2$), an amino group (for example, an unsubstituted amino group, a monoalkyl-, monoaralkyl-, monoalkenyl- or monoalkynylamino group, such as ethylamino, butylamino, octadecylamino, cyclohexylamino, benzylamino, diphenylmethylamino, naphthylmethylamino, phenethylamino, allylamino, 2-butenylamino, 3-butenylamino, cyclohexenylamino or propargylamino, etc., a monoarylamino group such as anilino, toluidino, anisidino, xylidino, p-nitrophenylamino, p-bromophenylamino or α-naphthylamino, etc., a monoheteroarylamino group, such as pyridylamino, quinolylamino, acridinylamino, benzothiazolylamino, triazinylamino, furylamino or thienylamino, etc., a mono-(substituted alkyl)amino group, such as β-(N,N-dimethylamino)ethylamino, β-methoxyethylamino, β-cyanoethylamino, β-chloroethylamino, ethoxycarbonylmethylamino, cyanomethylamino, ethoxymethylamino, ethylthiomethylamino, 4-(methylthio)-butylamino, trifluoromethylamino, 2-thiazolylmethylamino, (p-tolylsulfonyl)methylamino or 1,1-dimethyl-3-oxo-butylamino, etc., a monosilylamino group, such as trimethylsilylamino, triphenylsilylamino or trimethoxysilylamino, etc., a disubstituted amino group, such as diethylamino, dibenzylamino, diphenylamino, N-benzyl-N-ethylamino, N-ethyl-N-phenylamino or bis(β-methoxyethyl)amino, etc., or a cyclic amino group, such as morpholino, piperidino, piperazino, pyrrolidino or tetrahydroquinolino, etc.), an amido group (for example, a carbonylamino group, such as acetamido, trifluoroacetamido, cyclohexanecarboxamido, benzamido, α-pyridinecarboxamido, α-furancarboxamido, butoxycarbonylamino, (butylthio)carbonylamino or 3,3-diethylureido, etc., a thiocarbonylamino group, such as benzothioamido, 3,3-diethylthioureido, α-thienylthiocarbonylamino or butoxythiocarbonylamino, etc., a sulfonamido group, such as methanesulfonamido, p-toluenesulfonamido or dimethylaminosulfonylamino, etc., or an imidoylamino group, such as (N-phenylbenzimidoyl)amino, (N-phenyltrimethylacetoimidoyl)amino, (N-methylbenzimidoyl)amino, [N-(4-methoxyphenyl)benzimidoyl]amino or (N-phenyl-4-chlorobenzimidoyl)amino, etc.), an oxy group (for example, hydroxy, alkoxy, aralkyloxy, alkenyloxy, aryloxy, heteroaryloxy, alkenyloxy, alkynyloxy, substituted alkoxy, acyloxy or sulfonyloxy, in which the substituents can be one or more of those of the aryl group in $A_1$ and $A_2$) or a thio group (for example, a mercapto group, an alkylthio group such as ethylthio, butylthio or cyclohexylthio, an aralkylthio group, such as benzylthio, an alkenylthio group, such as allylthio, an alkynylthio group, such as propargylthio, an arylthio group, such as phenylthio or a heteroarylthio group, such as α-pyridylthio or 2-benzothiazolylthio, etc.).

However, at least one of $A_1$ and $A_2$ or of $A_1$ and $A_2$ combined represents an electron donating aryl group (i.e., an aryl group having an amino group, an oxy group such as alkoxy or a thio group such as alkylthio at a suitable position, wherein the term "suitable position" means the o- or p-position in the case of a phenyl group, the 2-, 4-, 5- or 7-position in the case of a 1-naphthyl group and the 1-, 3-, 6- or 8-position in the case of a 2-naphthyl group) or an electron donating heterocyclic group (a residue of a π-electron excess heteroaromatic ring as described in A. Albert, *Heterocyclic Chemistry*, Second Ed., Chapters 5 and 6, The Athlone Press (1968), or a heterocyclic residue containing ethylenic carbon-carbon bonds described in Chapters 8 and 9, A. Albert, supra, wherein the substitution position of the residue is that which can be conjugated with the hetero atom).

Examples of π-electron excess heteroaromatic rings (completely unsaturated heterocycles, having one or more of nitrogen, oxygen or sulfur as a hetero-element, and an excess of π-electrons elsewhere) are pyrrole, indole, carbazole, pyrazole, imidazole, furan, benzofuran, dibenzofuran, thiophene, benzothiophene, oxazole, thiazole and benzothiazole, etc. Examples of heterocyclic rings having ethylenic carbon-carbon bonds (partly hydrogenated 5- or 6-membered heteroaromatic rings or 6-membered cyclic compounds having an ethylenic carbon-carbon bond (which is easily hydrogenated) adjacent a hetero atom having an unshared electron pair, such as nitrogen, oxygen or sulfur) are 1,2,3,4-tetrahydroquinoline, indoline, phenothiazine, phenoxazine, julolidine and methylenedioxybenzene, etc.

Where Y represents an unsubstituted amino group, a monosubstituted amino group or an amido group, namely, where the formula (I) is the following formula (I'), formulae (III), (IV) and (V) are thought as tautomers of the formula (II'), in addition to the formula (II') which corresponds with formula (II). However, it is very difficult to decide which one of the formulae (II'), (III), (IV) and (V) is the compound prepared by the process of the present invention.

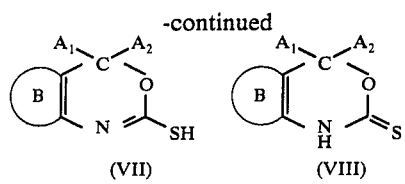

Where Y represents the above described unsubstituted amino group, monosubstituted amino group or amido group, all compounds prepared by the process of the present invention are represented by the formula (II), since the products are tautomeric and the chemical structure of them cannot be decided.

The process for preparing the thiazine derivatives of the present invention is illustrated specifically in the following. Although there are many processes for oxidizing thioamide derivatives represented by the formula (I), it is preferred to carry out the oxidation using metal oxides, such as lead dioxide, manganese dioxide, iron oxide, copper oxide, chromium oxide, cobalt oxide or nickel oxide, etc., quinones, such as chloranil (tetrachloroquinone) or tetracyanoquinone, etc., inorganic peroxides, such as hydrogen peroxide, etc., or organic peroxides, such as peracetic acid or perbenzoic acid, etc., as oxidizing agents under acid conditions (there are no restrictions on pH as long as the pH is below about 7) at about −10° C. to about 50° C. (at about 40° C. to about 100° C. in cases of using quinones) in order to produce the thiazine derivatives represented by the

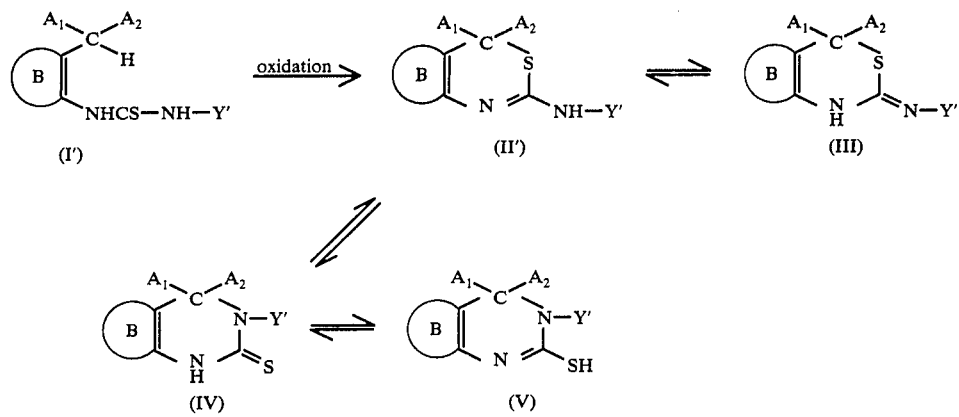

wherein Y' represents a residue resulting from the above described unsubstituted amino group, monosubstituted amino group or amido group by removal of —NH therefrom.

Further, where Y represents a hydroxyl group or a mercapto group, the following formula (VI) is thought as a tautomer in addition to the formula (II). However, the possibility of formulae (VII) and (VIII) existing can be ruled out based on IR-spectral data.

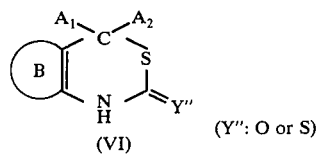

formula (II) in a high yield. Organic acids such as formic acid, acetic acid or propionic acid, etc., and inorganic acids, such as nitric acid, hydrochloric acid, sulfuric acid or phosphoric acid, etc., can be used to achieve the acidic conditions required. Lead dioxide and manganese dioxide are particularly preferred as oxidizing agents and acetic acid and nitric acid are particularly preferred as acids. In carrying out the reaction, the acids may be used as the solvent per se. However, solvents described in Yozai Pocket Handbook (edited by Yukigosei Kagaku Kyokai, published by Ohm Co.), for example, water, alcohols, such as methanol or ethanol, etc., ketones, such as acetone or methyl ethyl ketone, etc., aromatic hydrocarbons, such as benzene or toluene, etc., and halogenated hydrocarbons, such as chloroform or methylene dichloride, etc., can be used as solvents for diluting the reactants. Water and alcohols often give good results.

Although an amount of the oxidizing agents used depends upon the kind of oxidizing agent thereof, it is possible to use as a standard a range of from about 1 to about 5 (particularly, 1 to 3) times (equivalent ratio) of the thioamide derivatives as the raw material. These values can be suitably varied depending on the kind of thioamide derivative used. For example, in cases of using manganese dioxide, an amount of from about 1 to about 8 (particularly, 1 to 6) times (equivalent ratio) is preferred.

Further, although the reaction time will vary according to a temperature used, a range of from about 30 minutes to about 3 hours (particularly, 30 minutes to 2 hours) is preferred. In using manganese dioxide, it is sometimes necessary to react for 5 to 6 hours. Whether or not the reaction needs to be continued can be easily determined using paper chromatographic analysis of a portion of the reaction solution by measuring whether raw materials are present or not.

The thiazine derivatives of the present invention are useful as color formers for pressure-sensitive or heat-sensitive copying papers, light-sensitive papers, ultrasonic recording papers, electrostatic recording papers, electrothermic heat-sensitive recording papers, inks for stamping ribbons, inks for ball point pens, crayons, typewriter ribbons and pressure detecting papers, etc. Particularly, the thiazine derivatives of this invention have good resistance to light.

Examples of electron accepting materials (acid materials) are those which are used as developers for pressure-sensitive copying papers, such as the phenols described in Japanese Patent Publication No. 9309/65, clays (for example, acid clay), mineral acids, organic acids and phenols described in Japanese Patent Publication No. 33712/73, and phenol resins described in Japanese Patent Publication No. 20144/67.

The present invention will be illustrated in greater detail with reference to some examples thereof. However, the present invention is not to be construed as being limited to these examples. Unless otherwise indicated herein, all parts, percents, ratios and the like are by weight.

EXAMPLE 1

After 40 g of 4-diethylamino-2-(N'-pivaloylthioureido)-4',4''-bis-(dimethylamino)triphenylmethane was dissolved in 300 ml of 90% acetic acid, the solution was cooled with stirring and 20 g of lead dioxide was added thereto. After stirring at 5° to 20° C. for 1 hour, the mixture was poured into about 3 liters of ice-water and extracted twice, each time with 500 ml of benzene. After the benzene extract solution was washed with water, with a 1 to 2% aqueous solution of sodium hydroxide and then with water, it was dried with sodium sulfate. An oily product, which resulted on removal of the benzene by distillation under a reduced pressure, was dissolved in 200 ml of acetone, and 300 ml of methanol was added thereto. The solution was then cooled by which 4H-7-diethylamino-4,4-bis-(p-dimethylaminophenyl)-2-pivaloylamino-3,1-benzothiazine precipitated as bluish white crystals. The crystals were separated by filtration and dried. Yield: 25 g. After recrystallization with acetone, the melting point was 233°–236° C. The compound formed a blue color on contact with acid clay.

EXAMPLE 2

After 20 g of 4-diethylamino-2-(N'-phenylthioureido)-4',4''-bis-(dimethylamino)triphenylmethane was dissolved in 200 ml of 90% acetic acid, the solution was cooled with ice-water. After addition of 10 g of lead dioxide, the mixture was stirred at 5°–20° C. for 1 hour. It was then poured into 2 liters of ice-water. After extraction with benzene, the extract was washed with a 1 to 2% by weight aqueous solution of sodium hydroxide and then with water. After drying, benzene was removed by distillation under a reduced pressure. The resulting oil was dissolved in 50 ml of acetone. 50 ml of methanol was added thereto and the mixture was cooled, by which 4H-7-diethylamino-4,4-bis-(p-dimethylaminophenyl)-2-anilino-3,1-benzothiazine precipitated as white crystals. After separation by filtration, the crystals were dried. Yield: 10 g. Melting point: 256° to 259° C. The compound turned blue on contact with acid clay.

EXAMPLE 3

48 g of 4-dibenzylamino-2-(N'-pivaloylthioureido)-4',4''-bis-(dimethylamino)triphenylmethane was dissolved in 300 ml of 90% acetic acid and the solution was cooled with ice. After addition of 22 g of lead dioxide, the mixture was stirred at 5°–25° C. for 1 hour. The mixture was then poured into about 3 liters of ice-water and extracted with benzene. The extracted benzene phase was washed with water, with a 1 to 2% by weight aqueous solution of sodium hydroxide and then with water. It was then dried with sodium sulfate. After removal of the benzene by distillation under a reduced pressure, the residue oil was dissolved in 200 ml of acetic acid and 300 ml of methanol was added thereto. The solution was then cooled, by which 4H-7-dibenzylamino-4,4-bis-(p-dimethylaminophenyl)-2-pivaloylamino-3,1-benzothiazine precipitated as white crystals. Yield: 30 g. Melting point: 208°–212° C. The compound turned blue on contact with acid clay.

EXAMPLE 4

37 g of 4-diethylamino-2-(N'-pivaloylthioureido)-4',4''-bis-[N-ethyl-N-(p-tolyl)amino]triphenylmethane was dissolved in 300 ml of 90% acetic acid and the solution was cooled with ice water. 15 g of lead dioxide was then added incrementally. After stirring at 5°–25° C. for 1 hour, the mixture was poured into 1 liter of ice water and extracted with benzene. The extract was washed with water, with a 1 to 2% by weight aqueous solution of sodium hydroxide and with water. After drying, benzene was removed by distillation. The product was dissolved in 200 ml of petroleum ether and the solution was cooled, by which 4H-7-diethylamino-4,4-bis{p-[N-ethyl-N-(p-tolyl)amino]phenyl}-2-pivaloylamino-3,1-benzothiazine precipitated as white crystals. The precipitate was separated by filtration and dried. Yield: 25 g. Melting point: 158° to 162° C. The compound turned blue on contact with acid clay.

EXAMPLE 5

40 g of 4-dibenzylamino-2-(N'-isobutoxycarbonylthioureido)-4',4''-bis-(dimethylamino)triphenylmethane was dissolved in 300 ml of 90% acetic acid and the solution was cooled with ice. 15 g of lead dioxide was added thereto. After reaction at 5°–25° C. for 1 hour, the mixture was poured into 2 liters of ice-water and extracted with benzene. The benzene phase was washed with water, with a 1 to 2% by weight aqueous solution of sodium hydroxide and with water in turn. After drying, benzene was removed by distillation. The oily residue was dissolved in 200 ml of acetone and cooled, by which 4H-7-dibenzylamino-4,4-bis-(p-dimethylaminophenyl)-2-isobutoxycarbonylamino-3,1-benzothiazine precipitated as white crystals. Yield: 15 g. Melting point: 168°–171° C. The compound turned blue on contact with acid clay.

EXAMPLE 6

50 g of 5-methyl-2-(N'-pivaloylthioureido)-4',4'''-bis-(dimethylamino)triphenylmethane was dissolved in 150 ml of glacial acetic acid, and the solution was then diluted with 150 ml of methanol. After addition of 25 g of manganese dioxide, the mixture was stirred at 5°–25° C. for 4 hours. 500 ml of water was added thereto and the resulted precipitate was separated by filtration. The precipitate was dissolved in benzene and the solution was filtered, by which manganese residue was removed. The solution in benzene was washed with water and benzene was then removed by distillation. The residual oil was dissolved in 40 ml of acetone. 120 ml of methanol was added thereto and the solution was cooled, by which 4H-6-methyl-4,4-bis-(p-dimethylaminophenyl)-2-pivaloylamino-3,1-benzothiazine precipitated as white crystals. Yield: 38 g. After repeated recrystallization with acetone, the melting point was 236°–239° C. The compound turned bluish green on contact with acid clay.

EXAMPLE 7

23 g of 4-diethylamino-2-(thiobenzoylamino)-4',4''-bis-(dimethylamino)triphenylmethane was dissolved in 230 ml of glacial acetic acid, and the solution was cooled. 9 g of lead dioxide was added thereto. After stirring for 30 minutes, the solution was poured into an aqueous solution of sodium hydrosulfide (about 5% by weight) and extracted with benzene. After removal of lead sulfide by filtration, the extract was washed with water and dried. Benzene was removed by distillation and the residue was dissolved in a small amount of acetone. The solution was then filtered to remove the sulfur produced as a by-product. The filtrate was diluted with methanol and cooled, by which 4H-7-diethylamino-4,4-bis-(p-dimethylaminophenyl)-2-phenyl-3,1-benzothiazine precipitated as white crystals. Yield: 8 g. Melting point: 235°–237° C. The compound turned blue on contact with acid clay.

EXAMPLE 8

4H-7-diethylamino-4,4 -bis-(p-dimethylaminophenyl)-2-benzoylamino-3,1-benzothiazine (melting point: 231°–234° C.) was obtained in the same manner as in Example 1 except that 4-diethylamino-2-(N'-benzoylthioureido)-4',4''-bis-(dimethylamino)triphenylmethane was used instead of 4-diethylamino-2-(N'-pivaloylthioureido)-4',4''-bis-(dimethylamino)triphenylmethane. The compound turned blue on contact with acid clay.

EXAMPLE 9

4H-7-dimethylamino-4,4-bis-(9'-ethyl-3'-methylcarbazol-6'-yl)-2-pivaloylamino-3,1-benzothiazine (melting point: 297° to 299° C.) was obtained by oxidative ring-closure of [4-dimethylamino-2-(N'-pivaloylthioureido)-phenyl]-bis-(9-ethyl-3-methylcarbazol-6-yl)methane in the same manner as in Example 1. The compound turned blue on contact with acid clay.

EXAMPLE 10

4H-7-diethylamino-4-(p-diethylaminophenyl)-4-(9-ethylcarbazol-3-yl)-2-pivaloylamino-3,1-benzothiazine (melting point: 155°–158° C.) was obtained by oxidative ring-closure of [4-diethylamino-2-(N'-pivaloylthioureido)phenyl]-(4-diethylaminophenyl)-(9-ethylcarbazol-3-yl)methane in the same manner as in Example 1. The compound turned blue on contact with acid clay.

EXAMPLE 11

4H-7-diethylamino-4-(p-diethylaminophenyl)-4-(9'-ethylcarbazol-3'-yl)-2-anilino-3,1-benzothiazine (melting point: 148°–150° C.) was obtained by oxidative ring-closure of [4-diethylamino-2-(N'-phenylthioureido)-phenyl]-(4-diethylaminophenyl)-(9-ethylcarbazol-3-yl)methane in the same manner as in Example 1. The compound turned blue on contact with acid clay.

EXAMPLE 12

4H-6-methyl-4,4-bis-(p-dimethylaminophenyl)-2-ethoxycarbonylamino-3,1-benzothiazine (melting point: 198°–202° C.) was obtained by oxidative ring-closure of 5-methyl-2-(N'-ethoxycarbonylthioureido)-4',4''-bis-(dimethylamino)triphenylmethane in the same manner as in Example 1. The compound turned bluish green on contact with acid clay.

EXAMPLE 13

4H-7-diethylamino-4,4-bis-(p-dibenzylaminophenyl)-2-pivaloylamino-3,1-benzothiazine was obtained by oxidative ring-closure of 4-diethylamino-2-(N'-pivaloylthioureido)-4',4''-bis-(dibenzylamino)triphenylmethane in the same manner as in Example 1. The compound turned blue on contact with acid clay.

EXAMPLE 14

4H-6-methyl-4,4-bis-(p-dimethylaminophenyl)-2-benzoylamino-3,1-benzothiazine (melting point: 238°–240° C.) was obtained by oxidative ring-closure of 5-methyl-2-(N'-benzoylthioureido)-4',4''-bis-(dimethylamino)triphenylmethane in the same manner as in Example 1. The compound turned bluish green on contact with acid clay.

EXAMPLE 15

4H-6-methyl-4,4-bis-(p-dimethylaminophenyl)-2-(p-methoxybenzoylamino)-3,1-benzothiazine (melting point: 223° to 235° C.) was obtained by oxidative ring-closure of 5-methyl-2-[N'-(p-methoxybenzoyl)thioureido]-4',4''-bis-(dimethylamino)triphenylmethane in the same manner as in Example 1. The compound turned bluish green on contact with acid clay.

EXAMPLE 16

4H-6-methyl-4,4-bis-(p-dimethylaminophenyl)-2-acetylamino-3,1-benzothiazine (melting point: 212°–215° C.) was obtained by oxidative ring-closure of 5-methyl-2-(N'-acetylthioureido)-4',4''-bis-(dimethylamino)triphenylmethane in the same manner as in Example 6. The compound turned bluish green on contact with acid clay.

EXAMPLE 17

4H-6,8-dimethyl-4,4-bis-(p-dimethylaminophenyl)-2-pivaloylamino-3,1-benzothiazine (melting point: 272°–275° C.) was obtained by oxidative ring-closure of 3,5-dimethyl-2-(N'-pivaloylthioureido)-4',4''-bis-(dimethylamino)triphenylmethane in the same manner as in Example 6. The compound turned bluish green on contact with acid clay.

EXAMPLE 18

4H-6-methyl-4,4-bis-(p-dimethylaminophenyl)-2-isobutyrylamino-3,1-benzothiazine (melting point: 230°–231° C.) was obtained by oxidative ring-closure of 5-methyl-2-(N'-isobutyrylthioureido)-4',4''-bis-(dimethylamino)triphenylmethane in the same manner as in Example 1. The compound turned bluish green on contact with acid clay.

EXAMPLE 19

4H-6-methyl-4,4-bis-(p-dimethylaminophenyl)-2-butyrylamino-3,1-benzothiazine (melting point: 220°–224° C.) was obtained by oxidative ring-closure of 5-methyl-2-(N'-butyrylthioureido)-4',4''-bis-(dimethylamino)triphenylmethane in the same manner as in Example 6. The compound turned bluish green on contact with acid clay.

EXAMPLE 20

4H-6-methyl-4,4-bis-(p-dimethylaminophenyl)-2-valerylamino-3,1-benzothiazine (melting point: 183°–184° C.) was obtained by oxidative ring-closure of 5-methyl-2-(N'-valerylthioureido)-4',4''-bis-(dimethylamino)triphenylmethane in the same manner as in Example 6. The compound turned bluish green on contact with acid clay.

EXAMPLE 21

4H-6-methyl-4,4-bis-(p-dimethylaminophenyl)-2-octanoylamino-3,1-benzothiazine (melting point: 193°–195° C.) was obtained by oxidative ring-closure of 5-methyl-2-(N'-octanoylthioureido)-4',4''-bis-(dimethylamino)triphenylmethane in the same manner as in Example 1. The compound turned bluish green on contact with acid clay.

EXAMPLE 22

4H-6-methyl-4,4-bis-(p-dimethylaminophenyl)-2-decanoylamino-3,1-benzothiazine (melting point: 144°–147° C.) was obtained by oxidative ring-closure of 5-methyl-2-(N'-decanoylthioureido)-4',4''-bis-(dimethylamino)triphenylmethane in the same manner as in Example 1. The compound turned bluish green on contact with acid clay.

EXAMPLE 23

4H-6-methyl-4,4-bis-(p-dimethylaminophenyl)-2-dodecanoylamino-3,1-benzothiazine (melting point: 145°–147° C.) was obtained by oxidative ring-closure of 5-methyl-2-(N'-dodecanoylthioureido)-4',4''-bis-(dimethylamino)triphenylmethane in the same manner as in Example 1. The compound turned bluish green on contact with acid clay.

EXAMPLE 24

4H-6-methyl-4,4-bis-(p-dimethylaminophenyl)-2-tetradecanoylamino-3,1-benzothiazine was obtained by oxidative ring-closure of 5-methyl-2-(N'-tetradecanoylthioureido)-4',4''-bis-(dimethylamino)triphenylmethane in the same manner as in Example 1. This compound was light yellow and waxy at room temperature (about 20°–30° C.), and turned bluish green on contact with acid clay.

EXAMPLE 25

4H-6-methyl-4,4-bis-(p-dimethylaminophenyl)-2-hexadecanoyl-3,1-benzothiazine was obtained by oxidative ring-closure of 5-methyl-2-(N'-hexadecanoylthioureido)-4',4''-bis-(dimethylamino)triphenylmethane in the same manner as in Example 1. This compound was light yellow and waxy at room temperature, and turned bluish green on contact with acid clay.

EXAMPLE 26

4H-6-methyl-4,4-bis-(p-dimethylaminophenyl)-2-octadecanoylamino-3,1-benzothiazine was obtained by oxidative ring-closure of 5-methyl-2-(N'-octadecanoylthioureido)-4',4''-bis-(dimethylamino)triphenylmethane in the same manner as in Example 1. This compound was light yellow and waxy at room temperature, and turned bluish green on contact with acid clay.

EXAMPLE 27

4H-6-methoxy-4,4-bis-(p-dimethylaminophenyl)-2-pivaloylamino-3,1-benzothiazine was obtained by oxidative ring-closure of 5-methoxy-2-(N'-pivaloylthioureido)-4',4''-bis-(dimethylamino)triphenylmethane in the same manner as in Example 1. Melting point: 218°–222° C. The compound turned bluish green on contact with acid clay.

EXAMPLE 28

4H-7-dimethylamino-4,4-bis-(p-dimethylaminophenyl)-2-dimethylamino-3,1-benzothiazine was obtained by oxidative ring-closure of 2-(N',N'-dimethylthioureido)-4,4'4''-tris-(dimethylamino)triphenylmethane in the same manner as in Example 1. Melting point: above 300° C. The compound turned blue on contact with acid clay.

EXAMPLE 29

4H-7-diethylamino-4,4-bis-(p-dimethylaminophenyl)-2-phenoxyacetylamino-3,1-benzothiazine (melting point: 195°–198° C.) was obtained by oxidative ring-closure of 4-diethylamino-2-(N'-phenoxyacetylthioureido)-4',4''-bis-(dimethylamino)triphenylmethane in the same manner as in Example 1. The compound turned blue on contact with acid clay.

EXAMPLE 30

4H-7-diethylamino-4,4-bis-(p-dimethylaminophenyl)-2-methylthio-3,1-benzothiazine was obtained by oxidative ring-closure of 4-diethylamino-2-[(methylthio)thiocarbonylamino]-4',4''-bis-(dimethylamino)triphenylmethane in the same manner as in Example 1. This compound decomposed at about 240° C., and turned blue on contact with acid clay.

EXAMPLE 31

4H-6-nitro-4,4-bis-(p-dimethylaminophenyl)-2-pivaloylamino-3,1-benzothiazine was obtained by oxidative ring-closure of 5-nitro-2-(N'-pivaloylthioureido)-4',4''-bis-(dimethylamino)triphenylmethane in the same manner as in Example 1. This compound turned bluish green on contact with acid clay.

EXAMPLE 32

4H-6-chloro-4,4-bis-(p-dimethylaminophenyl)-2-ethoxycarbonylamino-3,1-benzothiazine was obtained by oxidative ring-closure of 5-chloro-2-(N'-ethoxycarbonylthioureido)-4',4''-bis-(dimethylamino)triphenylmethane in the same manner as in Example 1. The compound turned bluish green on contact with acid clay.

EXAMPLE 33

4H-6-ethoxy-4,4-bis-(p-dimethylaminophenyl)-2-methoxycarbonylamino-3,1-benzothiazine was obtained by oxidative ring-closure of 5-ethoxy-2-(N'-methoxycarbonylthioureido)-4',4''-bis-(dimethylamino)triphenylmethane in the same manner as in Example 1. The compound turned bluish green on contact with acid clay.

EXAMPLE 34

4H-7-diethylamino-4,4-bis-(p-dimethylaminophenyl)-2-methylsulfonylamino-3,1-benzothiazine (melting point: 280° to 282° C.) was obtained by oxidative ring-closure of 4-diethylamino-2-(N'-methylsulfonylthioureido)-4',4''-bis-(dimethylamino)triphenylmethane in the same manner as in Example 1. The compound turned blue on contact with acid clay.

EXAMPLE 35

4H-7-diethylamino-4,4-bis-(p-dimethylaminophenyl)-2-(p-tolylsulfonylamino)-3,1-benzothiazine (melting point: 300° to 303° C.) was obtained by oxidative ring-closure of 4-diethylamino-2-(N'-p-tolylsulfonylthioureido)-4',4''-bis-(dimethylamino)triphenylmethane in the same manner as in Example 1. The compound turned blue on contact with acid clay.

EXAMPLES 36–85

4H-7-diethylamino-4,4-bis-(p-dimethylaminophenyl)-2-(dimethylaminosulfonyl)amino-3,1-benzothiazine was obtained by oxidative ring-closure of 4-diethylamino-2-[N'-(dimethylaminosulfonyl)thioureido]-4',4''-bis-(dimethylamino)triphenylmethane in the same manner as in Example 1. The compound turned blue on contact with acid clay.

3,1-Benzothiazine compounds which were prepared by oxidative ring-closure of methane derivatives in the same manner as described in the above examples and colors formed on contact with acid clay are shown below.

| Example | Starting Material | Product | Color on Contact with Acid Clay |
|---|---|---|---|
| 36 | 4-Diethylamino-2-[N'-(dimethylcarbamoyl)-thioureido]-4',4''-bis-(dimethylamino)-triphenylmethane | 4H-7-Diethylamino-4,4-bis(p-dimethylaminophenyl)-2-(N',N'-dimethylureido)-3,1-benzothiazine | Blue |
| 37 | 4-Diethylamino-2-(N'-isobutylthioureido)-4',4''-bis(dimethylamino)triphenylmethane | 4H-7-Diethylamino-4,4-bis(p-dimethylaminophenyl-2-isobutylamino-3,1-benzothiazine | Blue |
| 38 | [4-Diethylamino-2-(N'-pivaloylthioureido)-phenyl]-bis(1-methyl-2-phenylindol-3-yl)-methane | 4H-7-Diethylamino-4,4-bis(1'-methyl-2'-phenylindol-3'-yl)-2-pivaloylamino-3,1-benzothiazine | Blue |
| 39 | 4-Dipropylamino-2-(N'-acetylthioureido)-4',4''-bis(dimethylamino)triphenylmethane | 4H-7-Dipropylamino-4,4-bis(p-dimethylaminophenyl)-2-acetylamino-3,1-benzothiazine | Blue |
| 40 | 4-Dibutylamino-2-(N'-acetylthioureido)-4',4''-bis(dimethylamino)triphenylmethane | 4H-7-Dibutylamino-4,4-bis(p-dimethylaminophenyl)-2-acetylamino-3,1-benzothiazine | Blue |
| 41 | 4-(N-methyl-N-benzylamino)-2-(N'-acetylthioureido)-4',4''-bis(dimethylamino)-triphenylmethane | 4H-7-(N-Methyl-N-benzylamino)-4,4-bis(p-dimethylaminophenyl)-2-acetylamino-3,1-benzothiazine | Blue |
| 42 | 4-[N-ethyl-(p-toluidino)]-2-(N'acetylthioureido)-4',4''-bis(dimethylamino)triphenylmethane | 4H-7-[N-Ethyl-(p-toluidino)]-4,4-bis-(p-dimethylaminophenyl)-2-acetylamino-3,1-benzothiazine | Blue |
| 43 | 4-bis(Cyanoethyl)-amino-2-(N'-pivaloylthioureido)-4',4''-bis:(dimethylamino)-triphenylmethane | 4H-7-bis(Cyanoethyl)-amino-4,4-bis(p-dimethylaminophenyl)-2-pivaloylamino-3,1-benzothiazine | Blue |
| 44 | 4-bis(Chloroethyl)-amino-2-(N'-pivaloyl-thioureido)-4',4'' bis(dimethylamino)-triphenylmethane | 4H-7-bis(Chloroethyl)-amino-4,4-bis(p-dimethylaminophenyl)-2-pivaloylamino-3,1-benzothiazine | Blue |
| 45 | 4-bis(Hydroxyethyl)-amino-2-(N'-pivaloyl-thioureido)-4',4''-bis-(diethylamino)-triphenylmethane | 4H-7-bis(Hydroxyamino-4,4-bis(p-diethylaminophenyl)-2-pivaloylamino-3,1-benzothiazine | Blue |
| 46 | 4,4',4''-tris(Diethylamino)-2-(N'-acetylureido)-2',2''-dimethyltriphenylmethane | 4H-7-Diethylamino-4,4-bis(2'-methyl-4'-diethylaminophenyl)-2-acetylamino-3,1-benzothiazine | Blue |
| 47 | 4,4',4''-tris(Diethylamino)-2-(N'-pivaloyl- | 4H-7-Diethylamino-4,4-bis(3'-methyl- | |

-continued

| Example | Starting Material | Product | Color on Contact with Acid Clay |
|---|---|---|---|
| | thioureido)-3',3''-dimethyltriphenyl-methane | 4'-diethylaminophenyl)-2-pivaloylamino-3,1-benzothiazine | |
| 48 | 4,4',4''-tris(Diethyl-amino-2-(N'-pivaloyl-thioureido)-2',2''-dichlorotriphenyl-methane | 4H-7-Diethylamino-4,4-bis(2'-chloro-4'-dimethylaminophenyl)-2-pivaloylamino-3,1-benzothiazine | Blue |
| 49 | 4,4',4''-tris(Diethyl-amino)-2-(N'-pivaloyl-thioureido)-3',3''-dichlorotriphenyl-methane | 4H-7-Diethylamino-4,4-bis(3'-chloro-4'-diethylaminophenyl)-2-pivaloylamino-3,1-benzothiazine | Blue |
| 50 | 4-Diethylamino-2-(N'-pivaloylthioureido)-2',2''-dimethoxy-4',4''-bis(dimethyl-amino)triphenylmethane | 4H-7-Diethylamino-4,4-bis(2'-methoxy-4'-dimethylamino-phenyl)-2-pivaloyl-amino-3,1-benzo-thiazine | Blue |
| 51 | 4-Diethylamino-2-(N'-pivaloylthioureido)-3',3''-dimethoxy-4',4''-bis(dimethyl-amino)triphenylmethane | 4H-7-Diethylamino-4,4-bis(3'-methoxy-4'-dimethylamino-phenyl)-2-pivaloyl-amino-3,1-benzo-thiazine | Blue |
| 52 | 4-Diethylamino-2-(N'-benzyloxycarbonylthio-ureido)-4',4''-bis-(dimethylamino)-triphenylmethane | 4H-7-Diethylamino-4,4-bis(p-dimethyl-aminophenyl)-2-benzyloxycarbonyl-amino-3,1-benzo-thiazine | Blue |
| 53 | [4-Diethylamino-2-(N'-pivaloylthioureido)-phenyl]-bis(4-dimethyl-aminonaphthyl)methane | 4H-7-Diethylamino-4,4-bis(4'-dimethyl-aminonaphthyl)-2-pivaloylamino-3,1-benzothiazine | Blue |
| 54 | 4-[N-Ethyl-N-(β-naphthyl)amino]-2-(N'-pivaloylthio-ureido)-4',4''-bis-(dimethylamino)-triphenylmethane | 4H-7-[N-Ethyl-N-(β-naphthyl)amino]4,4-bis(p-dimethylamino-phenyl)-2-pivaloyl-amino-3,1-benzo-thiazine | Blue |
| 55 | 4-Dimethylamino-2-(N'-pivaloylthioureido)-4',4''-bis(dipropyl-amino)triphenylmethane | 4H-7-Dimethylamino-4,4-bis(p-dipropyl-aminophenyl)-2-pivaloylamino-3,1-benzothiazine | Blue |
| 56 | 4-Dimethylamino-2-(N'-pivaloylthioureido)-4',4''-bis(dibutyl-amino)triphenylmethane | 4H-7-Dimethylamino-4,4-bis(p-dibutyl-aminophenyl)-2-pivaloylamino-3,1-benzothiazine | Blue |
| 57 | 4-Diphenethylamino-2-(N'-pivaloylthio-ureido)-4',4''-bis-(dimethylamino)-triphenylmethane | 4H-7-Diphenethylamino-4,4-bis(p-dimethyl-aminophenyl)-2-pivaloylamino-3,1-benzothiazine | Blue |
| 58 | 4-bis(p-Chlorobenzyl)-amino-2-(N'pivaloyl-thioureido)-4',4''-bis-(dimethylamino)-triphenylmethane | 4H-7-bis(p-Chloro-benzyl)amino-4,4-bis-(p-dimethylamino-phenyl)-2-pivaloyl-amino-3,1-benzo-thiazine | Blue |
| 59 | 4-bis(o-Chlorobenzyl)-amino-2-(N'-pivaloyl-thioureido)-4',4''-bis-(dimethylamino)-triphenylmethane | 4H-7-bis(o-Chloro-benzyl)amino-4,4-bis-(p-dimethylamino-phenyl)-2-pivaloyl-amino-3,1-benzo-thiazine | Blue |
| 60 | 4-bis(p-Isopropyl-benzyl)amino-2-(N'-pivaloylthioureido)-4',4''-bis-(dimethylamino)-triphenylmethane | 4H-7-bis(p-Isopropyl-benzyl)amino-4,4-bis-(p-dimethylamino-phenyl)-2-pivaloyl-amino-3,1-benzo-thiazine | Blue |
| 61 | 4-Diethylamino-5-methoxy-2-(N'-pivaloylthioureido)-4',4''-bis-(dimethylamino)-triphenylmethane | 4H-6-Methoxy-7-diethylamino-4,4-bis(p-dimethylamino-phenyl)-2-pivaloyl-amino-3,1-benzo-thiazine | Blue |
| 62 | 4-Diethylamino-2-(N'-pivaloylthioureido)-4',4''-bis[N-ethyl-(p-bromoanilino)]-triphenylmethane | 4H-7-diethylamino-4,4-bis{p[N-ethyl-(p-bromoanilino)]-phenyl}-2-pivaloyl-amino-3,1-benzo-thiazine | Blue |
| 63 | 4-Diethylamino-2-(p-methylthiobenzoyl-amino)4',4''-bis-(dimethylamino)- | 4H-7-Diethylamino-4,4-bis(p-dimethyl-aminophenyl)-2-(p-tolyl)-3,1-benzo- | Blue |

-continued

| Example | Starting Material | Product | Color on Contact with Acid Clay |
|---|---|---|---|
| | triphenylmethane | thiazine | |
| 64 | 4-Diethylamino-2-(o-methylthiobenzoyl-amino)-4',4''-bis-(dimethylamino)-triphenylmethane | 4H-7-Diethylamino-4,4-bis(p-dimethyl-aminophenyl)-2-(o-tolyl)-3,1-benzo-thiazine | Blue |
| 65 | 4-Diethylamino-2-(m-methylthiobenzoyl-amino)-4',4''-bis-(dimethylamino)-triphenylmethane | 4H-7-Diethylamino-4,4-bis(p-dimethyl-aminophenyl)-2-(m-tolyl)-3,1-benzo-thiazine | Blue |
| 66 | 4-Diethylamino-2-(p-chlorothiobenzoyl-amino)-4',4''-bis-(dimethylamino)-triphenylmethane | 4H-7-diethylamino-4,4-bis(p-dimethyl-aminophenyl)-2-(p-chlorophenyl)-3,1-benzothiazine | Blue |
| 67 | 4-Diethylamino-2-(m-chlorothiobenzoyl-amino)-4',4''-bis-(dimethylamino)-triphenylmethane | 4H-7-Diethylamino-4,4-bis(p-dimethyl-aminophenyl)-2-(m-chlorophenyl)-3,1-benzothiazine | Blue |
| 68 | 4-Diethylamino-2-(p-fluorothiobenzoyl-amino)-4',4''-bis-(dimethylamino)-triphenylmethane | 4H-7-Diethylamino-4,4-bis(p-dimethyl-aminophenyl)-2-(p-fluorophenyl)-3,1-benzothiazine | Blue |
| 69 | 4-Diethylamino-2-[(3-thienyl)thiocarbonyl-amino]-4',4''-bis-(dimethylamino)-triphenylmethane | 4H-7-Diethylamino-4,4-bis(p-dimethyl-aminophenyl)-2-(3-thienyl)-3,1-benzothiazine | Blue |
| 70 | 4-Diethylamino-2-(methoxythiocarbonyl-amino)-4',4''-bis-(dimethylamino)-triphenylmethane | 4H-7-Diethylamino-4,4-bis(p-dimethyl-aminophenyl)-2-methoxy-3,1-benzothiazine | Blue |
| 71 | 4-Diethylamino-2-[N'-(p-chlorophenyl)-thioureido]-4',4''-bis-(dimethylamino)-triphenylmethane | 4H-7-Diethylamino-4,4-bis(p-dimethyl-aminophenyl)-2-(p-chloroanilino)-3,1-benzothiazine | Blue |
| 72 | 4-Diethylamino-2-[N'-(p-dimethylamino-phenyl)thioureido]-4',4''-bis-(dimethylamino)-triphenylmethane | 4H-7-Diethylamino-4,4-bis(p-dimethyl-aminophenyl)-2-(p-dimethylaminoanilino)-3,1-benzothiazine | Blue |
| 73 | 4-Diethylamino-2-[N'-(p-nitrophenyl)-thioureido]-4',4''-bis(dimethylamino)-triphenylmethane | 4H-7-Diethylamino-4,4-bis(p-dimethyl-aminophenyl)-2-(p-nitroanilino)-3,1-benzothiazine | Blue |
| 74 | 4-Diethylamino-2-[N'-(p-tolyl)thioureido]-4',4''-bis(dimethyl-amino)triphenyl-methane | 4H-7-Diethylamino-4,4-bis(p-dimethyl-aminophenyl)-2-(p-toluidino)-3,1-benzothiazine | Blue |
| 75 | [4-Dimethylamino-2-(N'-pivaloylthio-ureido)-1-naphthyl]-bis(p-dimethylamino-phenyl)methane | 1H-6-Dimethylamino-1,1-bis(p-dimethyl-aminophenyl)-3-pivaloylamino-naphtho[2,1-d]-2,4-thiazine | Blue |
| 76 | [1-(N'-Acetylthio-ureido)-2-naphthyl]-bis(p-dimethylamino-phenyl)methane | 4H-4,4-bis(p-Dimethyl-aminophenyl)-2-acetyl-amino-naphtho[1,2-d]-3,1-thiazine | Green |
| 77 | 5-Phenyl-2-(N'-acetyl-thioureido)-4',4''-bis-(dimethylamino)-triphenylmethane | 4H-6-Phenyl-4,4-bis-(p-dimethylamino-phenyl)-2-acetylamino-3,1-benzothiazine | Green |
| 78 | [5,6,7,8-Tetrahydro-2-(N'-acetylthioureido)-1-naphthyl]-bis(p-dimethylaminophenyl)-methane | 1H-7,8,9,10-Tetra hydro-1,1-bis(p-dimethylaminophenyl)-3-acetylamino-naphtho-[2,1-d]2,4-thiazine | Green |
| 79 | [2-(N'-Pivaloylthio-ureido)-1-methylindol-3-yl]-bis-(p-dimethyl-aminophenyl)methane | 1H,1,1-bis(p-Dimethyl-aminophenyl)-3-pivaloylamino-5-methylindolino[2,3-d]-2,4-thiazine | Blue |
| 80 | [2-(N'-Pivaloylthio-ureido)furan-3-yl]-bis(p-dimethylamino-phenyl)methane | 1H-1,1-bis(p-Dimethyl-aminophenyl)-3-pivaloylamino-furo-[2,3-d]-2,4-thiazine | Green |
| 81 | {5-[N'-(N-Phenyl-trimethylaceto-imidoyl)thioureido]-2-methylthiazol-4-yl}-bis(p-dimethylamino-phenyl)methane | 7H-7,7-bis(p-Dimethyl-aminophenyl)-5-(N-phenyltrimethyl-acetoimidoyl)amino-2-methyl-thiazolo-[5,4-d]-6,4-thiazine | Green |

-continued

| Example | Starting Material | Product | Color on Contact with Acid Clay |
|---|---|---|---|
| 82 | 2-Anilino-6-diethyl-amino-9-(5-methyl-2-thiobenzoylamino-phenyl)xanthene | 2'-Anilino-6'-diethyl-amino-2-phenyl-6-methyl-spiro(4H-3,1-benzothiazine-4,9'-xanthene) | Purplish black |
| 83 | 7-Diethylamino-3-methyl-1-phenyl-4-[5-chloro-2-(2-furyl-thiocarbonylamino)-phenyl]-4H-chromeno-[2,3-c]-pyrazole | 6-Chloro-7'-diethyl-amino-2-(2-furyl)-3+-methyl-1'-phenyl-spiro(4H-3,1-benzo-thiazine-4,4'-[4H]-chromeno[2,3-c]-pyrazole) | Red |
| 84 | 7-Benzyloxy-2-phenyl-4-[2-(N'-ethoxy-carbonylthioureido)-4-diethylaminophenyl]-4H-chromene | 7'-Benzyloxy-2-ethoxy-carbonylamino-7-diethylamino-2'-phenyl-spiro(4H-3,1-benzo-thiazine-4,4'-[4H]-chromene) | Blue |
| 85 | 3-Diethylamio-7-methyl-11-[2-(N'-2-pyridylthioureido)-5-methoxyphenyl]-11H-benzo[b]thieno[3,2-b]-chromene | 3'-Diethylamino-6-methoxy-7'-methyl-2-(2-pyridylamino)-spiro(4H-3,1-benzo-thiazine-4,11'-[11H]-benzo[b]thieno[3,2-b]-chromene) | Purple |

For reference purposes, the products of the present invention produced in Examples 9, 11 and 78 to 85 are represented by the following formulae.

9.
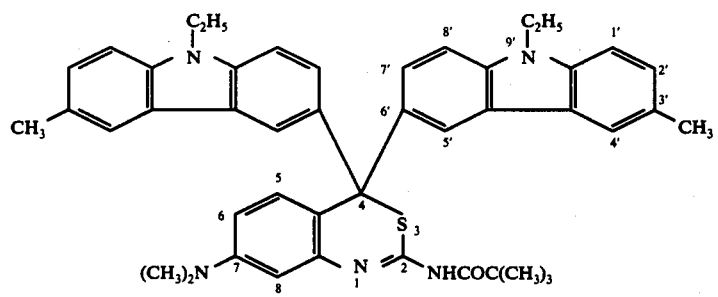

11.
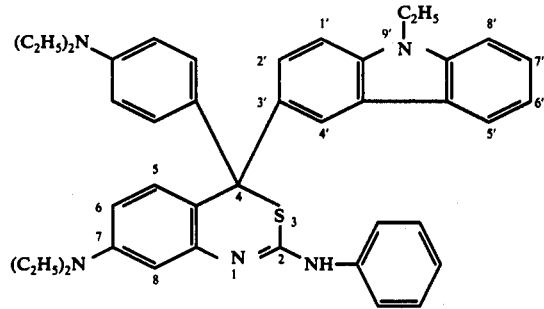

78.
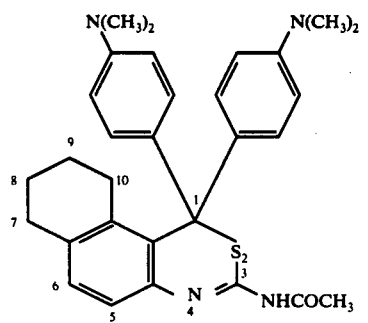

-continued
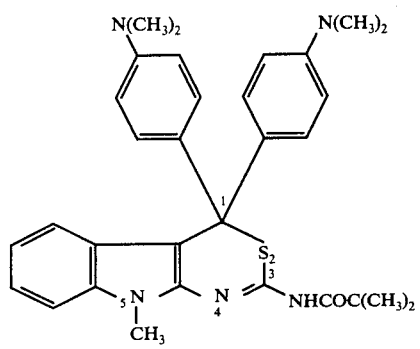
79.
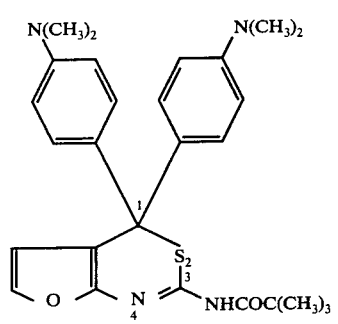
80.
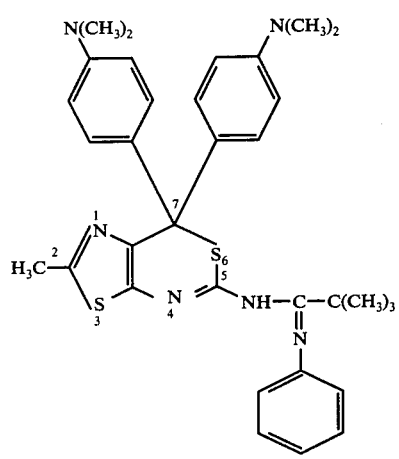
81.
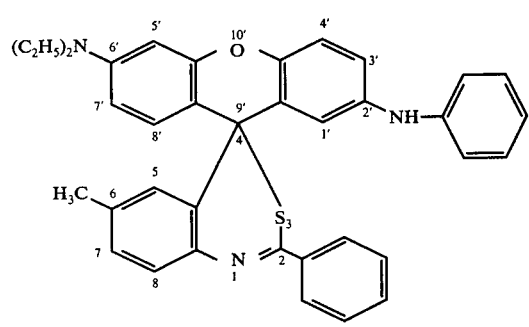
82.

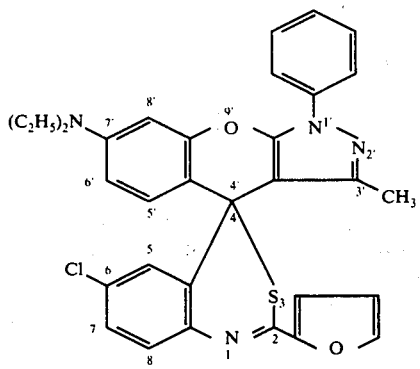

83.

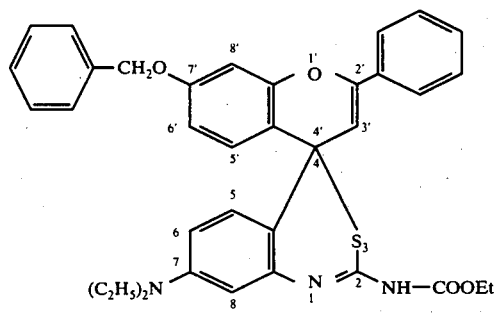

84.

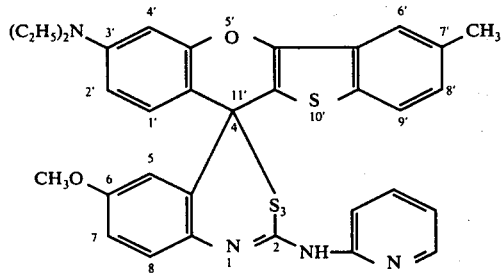

85.

While the invention has been described in detail with reference to specific embodiments thereof, it will be apparent to one skilled in the art that various changes and modifications can be made therein without departing from the spirit and scope thereof.

What is claimed is:

1. A process for preparing a thiazine derivative, which forms a color on contact with an electron-accepting material, represented by the formula (II):

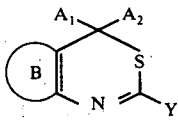

wherein $A_1$ and $A_2$, which may be the same of different, each is substituted with one or more substituents selected from the group consisting of methyl, ethyl, propyl, butyl, cyclohexyl, trifluoromethyl, α-methylbenzyl, α, α-dimethylbenzyl, 1,1-diphenylethyl, naphthylmethyl, phenethyl, fluorine, chlorine, bromine, iodine, methoxy, ethoxy, propoxy, butoxy, cyclohexyloxy, phenethyloxy, benzyloxy, naphthylmethyloxy, phenoxy, naphthoxy, α-pyridyloxy, γ-pyridyloxy, α-furyloxy, β-furyloxy, α-thienyloxy, β-thienyloxy, 2-pyrimidinyloxy, triazynyloxy allyloxy, isopropenyloxy, ethynyloxy, propargyloxy, acetonyloxy, phenacyloxy, ethoxycarbonylmethyloxy, N,N-diethylcarbamoylmethyloxy, acetonylmethyloxy, β-ethoxycarbonylethyloxy β-(N,N-dimethylamino)ethyloxy, β-methoxyethyloxy, β-cyanoethyloxy, β-chloroethyloxy, β-methanesulfonylethyloxy, acetoxy, benzoyloxy, 2-pyridinecarbonyloxy, ethoxycarbonyloxy, methanesulfonyloxy, p-toluenesulfonyloxy, an amino group selected from the group consisting of —NH₂, anilino, ethylamino, benzylamino, allylamino, propargylamino, cyclohexylamino, acetonylamino, ethoxycarbonylmethylamino, β-methoxyethylamino, dimethylamino, diethylamino, dibenzylamino, bis(ethoxymethyl)amino, bis(β-chloroethyl)amino, bis(β-cyanoethyl)amino, N-benzyl-N-ethylamino, N-ethyl-N-(p-tolyl)amino, N-benzyl-N-(β-ethoxyethyl)amino, N-methyl-N-phenacylamino, morpholino, piperidino, pyrrolidino, α-pyridylamino, β-furylamino, α- thienylamino, 2-pyrimidinylamino, dipropylamino, dibutylamino or N-ethyl-(p-bromoanilino), acetamido, benzamido, α-pyridinecarboxamido, butoxycarbonylamino, 3,3 diethylureido, N-ethylacetamido, p-toluenesulfonamido, N-butylmethanesulfonamido, benzothioamide, 3,3-diethylthioureido, methylthio, ethylthio, butylthio or benzylthio, or unsubstituted and is selected from the group consisting of phenyl, naphthyl, biphenyl, a five- or six-membered heterocyclic ring selected from the group consisting of p-julolidyl, 1,2,3,4-tetrahydroquinolin-6-yl, 3,3-dimethylindolin-5-yl, 3,4-methylenedioxyphenyl, 1,2-dimethyl-5-benzimidazolyl, 10-ethylphenothiazin-3-yl, 10-ethylphenoxazin-3-yl, 9-ethylcarbazol-3-yl, dibenzofuran-3-yl, dibenzothiophen-3-yl, quinolin-8-yl, 1,2-dimethylindol-3-yl, 1-ethylimidazol-3-yl, benzo{b} furan-3-yl, benzo{b} thiophen-3-yl, 1-ethylpyrrol-3-yl, 3-furyl, 3-thienyl, 2-thiazolyl, 2-benzoxazolyl, 2-pyridyl or 4-quinolyl, a heterocyclic formed by combining $A_1$ and $A_2$ represented by one of the following formulae:

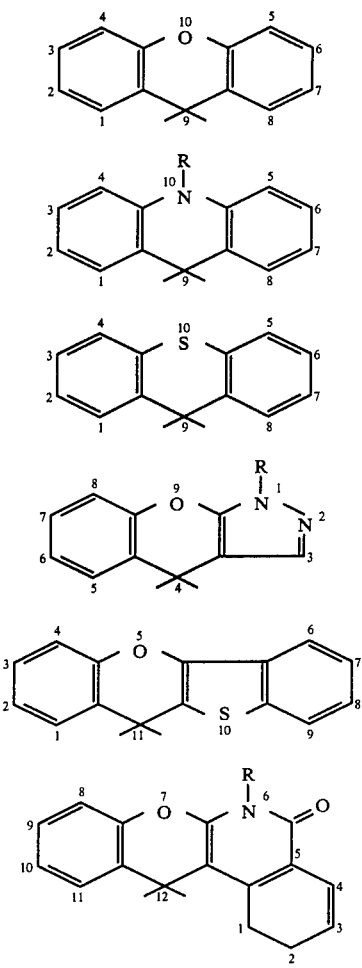

-continued

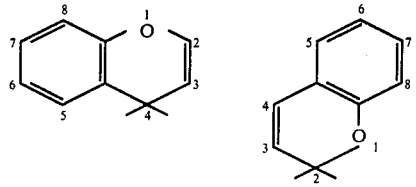

wherein R represents a straight or branched alkyl group having 1 to 4 carbon atoms, benzyl, phenethyl or phenyl, or a fluorene group formed by combining $A_1$ and $A_2$, at least one of $A_1$ and $A_2$ or the ring formed by combining $A_1$ and $A_2$ represents an electron donating aryl group having a said amino substituent group for $A_1$ and $A_2$ as a substituent or represents an electron donating heterocyclic group, respectively;

the ring B represents an aromatic hydrocarbon ring selected from the group consisting of a benzene ring, a naphthalene ring, a biphenyl ring or a tetralin ring or a heterocyclic ring selected from the group consisting of a pyrrole ring, a furan ring, a thiophene ring, an indole ring, a benzofuran ring, a benzothiophene ring, a carbazole ring, a dibenzofuran ring, a dibenzothiophene ring, a julolidine ring, a tetrahydroquinoline ring, a benzimidazole ring, a benzoxazole ring, a benzothiazole ring or a 1,3-benzo{d}dioxole ring; and Y represents a hydrogen atom, an aliphatic group, an aryl group, a heterocyclic group, an amino group, an amido group, an oxy group or a thio group said aliphatic group for Y is an unsubstituted straight chain, branched chain or cyclic alkyl of 1 to 18 carbon atoms, a straight chain, branched chain or cyclic alkyl of 1 to 18 carbons substituted with one or more of a halogen atom or a cyano group, an aralkyl group selected from the group consisting of benzyl, α-methylbenzyl, α,α-dimethylbenzyl, 1,1-diphenylethyl, naphthylmethyl or phenethyl, an alkenyl group selected from the group consisting of allyl, isopropenyl, 2-butenyl, cyclohexenyl or cinnamyl, or an alkynyl group selected from the group consisting of ethynyl, propargyl or 2-butynyl;

said aryl group for Y is selected from the group consisting of phenyl, naphthyl or biphenyl, each of which is unsubstituted or is substituted with one or more of said substituents for $A_1$ and $A_2$;

said heterocyclic group for Y is selected from the group consisting of p-julolidyl, 1,2,3,4-tetrahydroquinolin-6-yl, 3,3-dimethylindolin-5-yl, 3,4-methylenedioxyphenyl, 1,2-dimethyl-5-benzimidazolyl, 10-ethylphenothiazin-3-yl, 10-ethylphenoxazin-3-yl, 9-ethylcarbazol-3-yl, dibenzofuran-3-yl, dibenzothiophen-3-yl, quinolin-8-yl, 1,2-dimethylindol-3-yl, 1-ethylimidazol-3-yl, benzo{b}furan-3-yl, benzo{b}thiophen-3-yl, 1-ethylpyrrol-3-yl, 3-furyl, 3-thienyl, 2-thiazolyl, 2-benzoxazolyl, 2-pyridyl or 4-quinolyl, each of which is unsubstituted or is substituted with one or more of said substituents for $A_1$ and $A_2$;

said amino group for Y is selected from the group consisting of ethylamino, butylamino, octadecyl amino, cyclohexyl amino, benzylamino, diphenylmethylamino, naphthylmethylamino, phenethylamino, allyamino, 2-butenylamino, cyclohexenylamino, propargylamino, anilino, toluidino, anisidino, xylidino, p-nitrophenylamino, p-bromophenylamino, α-naphthylamino, pyridylamino, quinolylamino, acridinylamino, bennzothiazolyamino, triazinylamino, furylamino, thienylamino, β-(N,N-dimethylamino(ethylamino) β-methoxyethylamino, β-cyanoethylamino, β-chloro ethylamino, ethoxycarbonylmethylamino, cyanomethylamino, ethoxy methylamino, ethylthiomethylamino, 4-(methylthio)-butylamino, trifluoromethylamino, 2-thiazolylmethylamino, (p-tolylsulfonyl)methylamino, 1,1-dimethyl-3-oxobutylamino, trimethylsilylamino, triphenylsilylamino, trimethoxysilylamino, diethylamino, dibenzylamino, diphenylamino, N-benzyl-N-ethylamino, N-ethyl-phenylamino bis(β-methoxyethyl)amino, morpholino, piperidino, piperazino, pyrrolidino or tetrahydroquinolino;

said amido group for Y is selected from the group consisting of acetamido, trifluoroacetamido, cyclohexanecarboxamido, benzamido, α-pyridinecarboxamido, α-furancarboxamido, butoxycarbonylamino, (butylthio) carbonylamino, 3,3-diethylureido, benzothioamido, 3,3-diethylthioureido, α-thienylthiocarbonylamino, butoxythiocarbonylamino, methanesulfonamido, p-toluenesulfonamido, dimethylaminosulfonylamino, (N-phenylbenzimidoyl)amino, (N-phenyl-trimethylacetoimidoyl)amino, (N-methylbenzimidoyl)amino {N-(4-methoxyphenyl)benzimidoyl}amino, (N-phenyl-4-chlorobenzimidoyl)-amino, pivaloylamino, isobutoxycarbonylamino, ethoxycarbonylamino, isobutyrylamino, butyrylamino, valerylamino, octanoylamino, decanoylamino, dodecanoylamino, tetradecanoylamino, octadecanoylamino, phenoxyacetylamino, methoxycarbonylamino or benzyloxycarbonylamino;

said oxy group for Y is selected from the group consisting of hydroxy or methoxy, each of which is unsubstituted or is substituted with one or more of said substituents for $A_1$ and $A_2$; and said thio group for Y is selected from the group consisting of methylthio, ethylthio, butylthio, cyclohexylthio, benzylthio, allylthio, propargylthio, phenylthio, α-pyridylthio or 2-benzothiazolylthio; which comprises oxidizing a thioamide derivative represented by the formula (I):

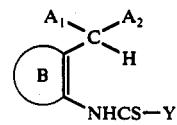

wherein $A_1$, $A_2$, ring B, and Y are as described above with an oxidizing agent selected from the group consisting of a metal oxide, a quinone, an inorganic peroxide or an organic peroxide under acid conditions at a temperature of about −10° C. to about 50° C. for all oxidizing agents except the quinone and at a temperature of about 40° C. to about 100° C. for the quinone.

2. The process of claim 1, wherein
said aliphatic group for Y is methyl, ethyl, propyl, butyl, hexyl, octyl, dodecyl, octadecyl, cyclopentyl, cyclohexyl, benzyl, α-methylbenzyl, α,α-dimethylbenzyl, 1, 1-diphenylethyl, naphthylmethyl, phenylethyl, allyl, isopropenyl, 2-butenyl, cyclohexenyl, cinnamyl, ethynyl, propargyl or 2-butynyl.

3. The process of claim 1, wherein
said aryl for Y is unsubstituted and is phenyl, naphthyl or biphenyl.

4. The process of claim 1, wherein
said heterocyclic group for Y is unsubstituted and is p-julolidyl, 1, 2, 3, 4-tetrahydroquinolin-6-yl, 3,3-dimethylindolin-5-yl, 3,4-methylenedioxyphenyl, 1,2-dimethyl-5-benzimidazolyl, 10-ethylphenothiazin-3-yl, 10-ethylphenoxazin-3-yl, 9-ethylcarbazol-3-yl, dibenzofuran-3-yl, dibenzothiophen-3-yl, quinolin-8-yl, 1,2-dimethylindol-3-yl, 1-ethylimidazol-3-yl, benzo[b]furan-3-yl, benzo[b]thiophen-3-yl, 1-ethylpyrrol-3-yl, 3-furyl, 3-thienyl, 2-thiazolyl, 2-benzoxazolyl, 2-pyridyl or 4-quinolyl.

5. The process of claim 1, wherein
said amido group for Y is acetamido, trifluoroacetamido, cyclohexanecarboxamido, benzamido, α-pyridinecarboxamido, α-furancarboxamido, butoxycarbonylamino, (butylthio) carbonylamino, 3, 3-diethylureido, benzothioamido, 3,3-diethylthioureido, α-thienylthiocarbonylamino, butoxythiocarbonylamino, methanesulfonamido, p-toluenesulfonamido, dimethylaminosulfonylamino, (N-phenylbenzimidoyl) amino, (N-phenyl-trimethylacetoimidoyl) amino, (N-methylbenzimidoyl) amino [N-(4-methoxyphenyl)benzimidoyl] amino or (N-phenyl-4-chlorobenzimidoyl)-amino.

6. The process of claim 1, wherein
said amino for Y is ethylamino.

7. The process of claim 1, wherein said ring B is a benzene ring.

8. The process of claim 1, wherein
said oxy group for Y is a hydroxy group; and
said thio group for Y is a mercapto group.

9. The process of claim 1, wherein said electron donating heterocyclic group is a residue of a π-electron excess hetero aromatic ring or a heterocyclic residue containing an ethylenic carbon-carbon bond wherein the substitution position of the heterocyclic residue is such that conjugation with the hetero atom can exist.

* * * * *